US010604460B2

(12) United States Patent
Sofranko et al.

(10) Patent No.: US 10,604,460 B2
(45) Date of Patent: Mar. 31, 2020

(54) OXIDATIVE COCRACKING OF HYDROCARBONS TO OLEFINS

(71) Applicant: EcoCatalytic Inc., Monmouth Junction, NJ (US)

(72) Inventors: John A. Sofranko, Monmouth Junction, NJ (US); Royce Macwan, Monmouth Junction, NJ (US); Elena Y. Chung, Monmouth Junction, NJ (US); C. Andrew Jones, Monmouth Junction, NJ (US)

(73) Assignee: EcoCatalytic Inc., Monmouth Junction, NJ (US)

( * ) Notice: Subject to any disclaimer, the term of this patent is extended or adjusted under 35 U.S.C. 154(b) by 0 days.

(21) Appl. No.: 16/343,138

(22) PCT Filed: Oct. 19, 2017

(86) PCT No.: PCT/US2017/057294
§ 371 (c)(1),
(2) Date: Apr. 18, 2019

(87) PCT Pub. No.: WO2018/075713
PCT Pub. Date: Apr. 26, 2018

(65) Prior Publication Data
US 2019/0315667 A1  Oct. 17, 2019

Related U.S. Application Data

(60) Provisional application No. 62/419,741, filed on Nov. 9, 2016, provisional application No. 62/409,903, filed on Oct. 19, 2016.

(51) Int. Cl.
*C07C 5/42* (2006.01)
*B01J 8/02* (2006.01)
(Continued)

(52) U.S. Cl.
CPC ............ *C07C 5/42* (2013.01); *B01J 8/025* (2013.01); *B01J 8/24* (2013.01); *C07C 4/025* (2013.01);
(Continued)

(58) Field of Classification Search
CPC .................... C07C 5/42; C07C 5/333
See application file for complete search history.

(56) References Cited

U.S. PATENT DOCUMENTS

| 4,283,583 A | 8/1981 | Velenyi et al. |
| 4,347,395 A * | 8/1982 | Chu ............ C07C 2/00 585/415 |

(Continued)

FOREIGN PATENT DOCUMENTS

| WO | 2016049144 A1 | 3/2016 |
| WO | 2016209811 A1 | 12/2016 |
| WO | 2018005456 A1 | 1/2018 |

OTHER PUBLICATIONS

International Search Report and Written Opinion for International Application No. PCT/US2017/057294, dated Jan. 12, 2018, 6 pages.
(Continued)

*Primary Examiner* — Michelle Stein
(74) *Attorney, Agent, or Firm* — RatnerPrestia

(57) ABSTRACT

Aspects of the invention relate to producing olefins by oxidative dehydrogenation cocracking of a hydrocarbon feed. In one embodiment, the method includes oxidative cocracking a hydrocarbon feed comprised of at least one alkane having a carbon chain of five or more and at least one alkane having a carbon chain of four or less by contacting the hydrocarbon feed with a metal oxide, such that the cracking of the at least one alkane having a carbon chain of four or less produces olefins and is exothermic, and the cracking of the at least one alkane having a carbon chain of five or more produces olefins and is endothermic. The
(Continued)

method further includes utilizing the energy produced from the exothermic cracking of the alkane having a carbon chain of four or less for the endothermic cracking of the alkane having a carbon chain of five or more, and collecting the product.

19 Claims, 10 Drawing Sheets

(51) Int. Cl.
*B01J 8/24* (2006.01)
*C07C 4/02* (2006.01)
*C07C 11/04* (2006.01)
*C07C 11/06* (2006.01)

(52) U.S. Cl.
CPC ..... *B01J 2219/00907* (2013.01); *C07C 11/04* (2013.01); *C07C 11/06* (2013.01); *C07C 2523/10* (2013.01); *C07C 2529/40* (2013.01)

(56) References Cited

U.S. PATENT DOCUMENTS

| | | | |
|---|---|---|---|
| 4,737,595 A | 4/1988 | Jones et al. | |
| 4,742,180 A | 5/1988 | Gaffney | |
| 5,019,663 A * | 5/1991 | Chou | C07C 2/00 585/415 |
| 5,811,622 A * | 9/1998 | Oroskar | C07C 5/42 585/617 |
| 7,491,315 B2 | 2/2009 | Eng | |
| 9,056,308 B2 | 6/2015 | Choo et al. | |
| 2004/0068153 A1 * | 4/2004 | Allison | B01J 23/10 585/660 |
| 2004/0171894 A1 * | 9/2004 | Colman | B01J 8/0242 568/959 |
| 2008/0177117 A1 * | 7/2008 | Benderly | C07C 5/48 585/324 |
| 2016/0318828 A1 | 11/2016 | Washburn et al. | |
| 2017/0226030 A1 | 8/2017 | Li et al. | |
| 2017/0247803 A1 | 8/2017 | Sofranko | |

OTHER PUBLICATIONS

International Preliminary Report on Patentability and Written Opinion for International Application No. PCT/US2017/057294, dated Apr. 23, 2019, 6 pages.
Ullman's Encyclopedia of Industrial Chemistry, Ethylene, vol. 13, pp. 465-529, 2012.
Edwards, et al., "The OXCO Process, A New Concept for the Production of Olefins From Natural Gas", Fuel, 1992, vol. 71, pp. 325-334.
Almutairi, "The Role of Lewis and Brønsted Acidity for Alkane Activation Over Zeolites", University of Technology, Published Jan. 1, 2013, 162. pages.
Krasnobaeva et al., "Synthesis and Properties of Inorganic Compounds. Praseodymium-Containing Catalysts for Oxidative Dehydrogenation of Organic Compounds", Russian Journal of Inorganic Chemistry, 2017, vol. 62, No. 7, pp. 879-885.
Narasimharao et al., Catalytic Oxidative Cracking of Propane Over Nanosized Gold Supported $Ce_{0.5}Zr_{0.5}O_2$ Catalysts, Catal. Lett., 2013, vol. 143, pp. 1074-1084.
Liu et al., "Light Alkenes Preparation by the Gas Phase Oxidative Cracking or Catalytic Oxidative Cracking of High Hydrocarbons", Catalysis Letters, 2004, vol. 94, Nos. 1-2, pp. 31-36.
Boyadjian et al., "Catalytic Oxidative Cracking of Hexane as a Route to Olefins", Applied Catalysis A: General, 2010, vol. 372, pp. 167-174.
Liu et al., "Production of Light Alkenes With Low $CO_2$ Emission From Gas Phase Oxidative Cracking (GOC) of Hexane", React. Kinet. Catal. Lett., 2004, vol. 81, No. 2, pp. 203-209.
Alwadood et al., "Kinetics of Oxidative Crackling of n-Hexane to Olefins Over $VO_x/Ce$—$Al_2O_3$ Under Gas Phase Oxygen-Free Environment", AIChE Journal, 2016, 9 pages.
Allfanti et al., "Oxidation of Ethane on High Specific Surface $SmCoO_3$ and $PrCoO_3$ Perovskites", Catalysis Today, 2009, vol. 143, pp. 309-314.
Tsang, "The Oxidative Cracking of Hydrocarbon Fuels", 2010, 48th AIAA Aerospace Sciences Meeting Including the New Horizons Forum and Aerospace Exposition, 1 page.
Arean et al., Measuring the Brønsted Acid Strength of Zeolites—Does it Correlate With the O—H Frequency Shift Probed by a Weak Base?, Phys. Chem., 2014, vol. 16, pp. 10129-10141.
Eng et al., :"A Catalytic Cracking Process for Ethylene and Propylene From Paraffin Stream the Advanced Catalytic Olefins (ACO) Process", 2007 Spring National Meeting, Apr. 2007, 13 pages.
Boyadjian et al., "Catalytic Oxi-Cracking as a Route to Olefins—Efficient Mo—LiMgO Catalysts for Hexane Conversion", Catalytic Processes and Materials, Faculty of Science and Technology, University of Twente, 1 page . Mar. 3, 2008.
Boyadjian et al., "Production of $C_3/C_4$ Olefins from n-Hexane: Conceptual Design of a Catalytic Oxidative Cracking Process and Comparison to Steam Cracking", Ind. Eng. Chem. Res., 2011, vol. 50, pp. 342-351.
Sofranko et al., "Natural Gas to Gasoline: The ARCO GTG Process", Symposium on Methane Activation, Conversion and Utilization, International Congress of Pacific Basin Societies, Dec. 17-20, 1989, pp. 152-154.
Dong, "Advanced Technology Development Reducing $CO_2$ Emissions", SK Energy Institute of Technology, 2013, 13 pages.

* cited by examiner

OXIDATIVE COCRACKING OF HYDROCARBONS TO OLEFINS

CROSS REFERENCE TO RELATED APPLICATIONS

The present application is the national phase of International Application No. PCT/US2017/057294, filed Oct. 19, 2017, which claims priority to and benefit of U.S. Provisional Patent Application No. 62/409,903, filed on Oct. 19, 2016, and U.S. Provisional Patent Application No. 62/419,741, filed on Nov. 9, 2016, the disclosures of each of which are incorporated herein by reference in their entirety for all purposes.

FIELD OF THE INVENTION

The present invention relates to methods, systems, and apparatuses for producing olefins by oxidative dehydrogenation cocracking of a hydrocarbon feed.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of global olefin production may come from the high temperature steam cracking of naphtha or ethane and propane. The steam cracking process, which utilizes furnaces, is highly energy intensive, and 1.5 to 2 tons of carbon dioxide are produced for every ton of olefin product.

Natural gas production from shale deposits has dramatically increased supply in recent years. As a result of the continued global demand for olefins and the potential for a new growing supply of ethane and propane available in natural gas liquids from shale deposits, interest has risen around expanding the capacity of ethylene and propylene derived from these new sources. However, there are many challenges associated with the processes for deriving ethylene and propylene from natural gas. For example, cracking ethane and propane is highly endothermic, requiring significant amounts of energy to facilitate the production of olefins. As stated in Ullmann's Encyclopedia of Industrial Chemistry, as the alkane chain length increases, the heat of formation approaches 1800 kJ/kg. Ethylene, 13 ULLMANN'S ENCYCLOPEDIA OF INDUSTRIAL CHEMISTRY 465, 476 (Viley-VCH Verlag GmbH & Co. KGaA, 2012). Thus, "[e]thane, the most refractory alkane besides methane, has the most endothermic heat of cracking, +4893 kJ/kg." Id. In addition, olefin production from natural gas liquids is often limited by several over-oxidation pathways.

Additionally, technology has not yet advanced to enable cheap transportation of natural gas to many global regions. Accordingly, although natural gas production from shale deposits has dramatically increased in a few select regions, the petrochemical industry in other regions of the world relies heavily on the production of ethylene and propylene from naphtha.

Accordingly, there is a long standing need for improved systems and methods for efficiently producing olefins from hydrocarbon feeds, such as hydrocarbon feeds including naphtha.

SUMMARY OF THE INVENTION

Aspects of the invention relate to methods, systems, and apparatuses for producing olefins by oxidative dehydrogenation cocracking of a hydrocarbon feed.

In accordance with one aspect of the invention, a method is provided for producing one or more olefins by oxidative dehydrogenation cocracking of a hydrocarbon feed. The method includes the steps of cocracking a hydrocarbon feed comprised of at least one alkane having a carbon chain of five or more and at least one alkane having a carbon chain of four or less by contacting the hydrocarbon feed with a metal oxide, such that the oxidative dehydrogenation cracking of the at least one alkane having a carbon chain of four or less produces one or more olefins and is exothermic, and the cracking of the at least one alkane having a carbon chain of five or more produces one or more olefins and is endothermic. The method further includes the steps of utilizing the energy produced from the exothermic oxidative dehydrogenation cracking of the at least one alkane having a carbon chain of four or less for the endothermic cracking of the at least one alkane having a carbon chain of five or more, and collecting a product from the cocracking of the hydrocarbon feed.

According to another aspect of the invention, a method is provided for producing one or more olefins by oxidative dehydrogenation cracking of a hydrocarbon feed comprising at least one alkane. The method comprises the step of cracking a hydrocarbon feed comprised of at least one alkane having a carbon chain of five or more by contacting the hydrocarbon feed with a metal oxide comprised of an oxide of praseodymium to produce one or more olefins.

In accordance with yet a further aspect of the invention, a system is provided for cocracking of a hydrocarbon feed comprised of two or more alkanes. The system includes a reactor containing a metal oxide therein, the metal oxide being comprised of an oxide of praseodymium and configured for cocracking at least one alkane having a carbon chain of five or more and at least one alkane having a carbon chain of four or less by oxidative dehydrogenation cracking to produce one or more olefins.

Various aspects of the invention may be summarized as follows:

Aspect 1: A method of producing one or more olefins by oxidative dehydrogenation cocracking of a hydrocarbon feed, the method comprising:

cocracking a hydrocarbon feed comprised of at least one alkane having a carbon chain of five or more and at least one alkane having a carbon chain of four or less by contacting the hydrocarbon feed with a metal oxide, such that the cracking of the at least one alkane having a carbon chain of four or less produces one or more olefins and is exothermic, and the cracking of the at least one alkane having a carbon chain of five or more produces one or more olefins and is endothermic;

utilizing the energy produced from the exothermic cracking of the at least one alkane having a carbon chain of four or less for the endothermic cracking of the at least one alkane having a carbon chain of five or more; and collecting a product from the cocracking of the hydrocarbon feed.

Aspect 2. The method of aspect 1, wherein cocracking of the hydrocarbon feed is performed at a temperature of greater than 500° C. and less than 1000° C. and wherein the product has a composition comprising at least 50% by weight of ethylene, propylene, or a combination thereof.

Aspect 3. The method of aspect 1, wherein cocracking of the hydrocarbon feed is performed at a temperature of greater than 600° C. and less than 850° C. and wherein the product has a composition comprising at least 40% by weight of ethylene, propylene, or a combination thereof.

Aspect 4. The method of aspect 1, wherein cocracking of the hydrocarbon feed is performed at a temperature of greater than 600° C. and less than 850° C. and wherein the product has a composition comprising at least 65% by weight of olefins.

Aspect 5. The method of aspect 1, wherein cocracking of the hydrocarbon feed is performed at a temperature of greater than 600° C. and less than 750° C. and wherein the product has a composition comprising at least 65% by weight of olefins.

Aspect 6. The method of any of aspects 1-5, wherein the at least one alkane having a carbon chain of four or less comprises ethane, and the at least one alkane having a carbon chain of five or more comprises naphtha.

Aspect 7. The method of aspect 6, wherein the hydrocarbon feed has a weight ratio of ethane to naphtha of from 3:10 to 9:10.

Aspect 8. The method of aspect 7, wherein the weight ratio of ethane to naphtha is from 3:10 to 6:10.

Aspect 9. The method of aspect 8, wherein the weight ratio of ethane to naphtha is from 3:10 to 4:10.

Aspect 10. The method of any of aspects 1-9, wherein the energy theoretically produced from the exothermic oxidative dehydrogenation of the at least one alkane having a carbon chain of four or less ranges from 0% to 10% greater than the energy theoretically required for the endothermic cracking of the at least one alkane having a carbon chain of five or more.

Aspect 11. The method of any of aspects 1-10, where the metal oxide comprises at least one element selected from the group consisting of oxides of La, Ce, Pr, Tb, Nd, and Dy.

Aspect 12. The method of any of aspects 1-11, wherein the metal oxide further comprises at least one promoter selected from the group consisting of Na, Li, Ca, Mg, Sr, or Ba.

Aspect 13. The method of any of aspects 1-10 and 12, wherein the metal oxide for cocracking the hydrocarbon feed is comprised of oxides of Pr.

Aspect 14. A method of producing one or more olefins by oxidative dehydrogenation cracking of a hydrocarbon feed comprising at least one alkane, the method comprising:
cracking a hydrocarbon feed comprised of at least one alkane having a carbon chain of five or more by contacting the hydrocarbon feed with a metal oxide comprised of praseodymium oxide to produce one or more olefins; and
collecting a product from the cracking of the hydrocarbon feed.

Aspect 15. The method of aspect 14, further comprising cracking at least one alkane having a carbon chain of four or less to exothermically produce one or more olefins concurrently with the cracking of the at least one alkane having a carbon chain of five or more to produce one or more olefins.

Aspect 16. The method of aspect 14, wherein the hydrocarbon feed further comprises at least one alkane having a carbon chain of four or less to exothermically produce one or more olefins, the energy produced from the exothermic cracking of the at least one alkane having a carbon chain of four or less being greater than the energy theoretically required for the endothermic cracking of the at least one alkane having a carbon chain of five or more.

Aspect 17. The method of any of aspects 14-16, wherein the metal oxide further comprises at least one promoter selected from the group consisting of Na, Li, Ca, Mg, Sr, or Ba.

Aspect 18. The method of any of aspects 14-17, wherein the metal oxide is employed in combination with a zeolite.

Aspect 19. The method of aspect 18, wherein the zeolite has a composition in accordance with general formula: $M_{2/n}O.Al_2O_3.ySiO_2.wH_2O$, where y varies from 2 to 1,000,000,000, M is a positively charged element for balancing the charge of the zeolite and may include protons, alkaline metals, alkaline earth metals or other elements known to those skilled in the art, n represents the cation valence and w represents the number of water molecules per zeolite unit structure, such that, at least 5% of n is due to proton charge.

Aspect 20. The method of aspect 18, wherein the zeolite has a composition in accordance with general formula: $M_{2/n}O.Al_2O_3.ySiO_2.wH_2O$ where y is from 4 to 35, M is a positively charged element for balancing the charge of the zeolite and may include protons, alkaline metals, alkaline earth metals or other elements known to those skilled in the art, n represents the cation valence and w represents the number water molecules per zeolite unit structure, such that, at least 5% of n is due to proton charge.

Aspect 21. The method of any of aspects 18-20, wherein the zeolite is ZSM-5.

Aspect 22. A system for cocracking of a hydrocarbon feed comprised of two or more alkanes comprising:
a reactor containing a metal oxide therein, the metal oxide being comprised of praseodymium oxide and configured for cocracking at least one alkane having a carbon chain of five or more and at least one alkane having a carbon chain of four or less by oxidative dehydrogenation cracking to produce one or more olefins.

Aspect 23. The system of aspect 22, further comprising at least one inlet for supplying at least one hydrocarbon feed stream coupled to the reactor, the hydrocarbon feed stream comprising the at least one alkane having a carbon chain of five or more and the at least one alkane having a carbon chain of four or less.

Aspect 24. The system of aspect 23, wherein the at least one alkane having a carbon chain of five or more and the at least one alkane having a carbon chain of four or less are concurrently cocracked within the same reactor.

Aspect 25. The system of any of aspects 22-24, wherein the reactor comprises a riser configured to facilitate contact of the hydrocarbon feed and the metal oxide.

Aspect 26. The system of any of aspects 22-25, wherein the reactor consists of a single riser, the riser configured to facilitate contact of the hydrocarbon feed and metal oxide.

Aspect 27. The system of any of aspects 22-25, wherein the reactor comprises at least a first riser and a second riser, the first riser configured for oxidative dehydrogenation of the at least one alkane having a carbon chain of five or more, the second riser configured for oxidative dehydrogenation of the at least one alkane having a carbon chain of four or less.

Aspect 28. The system of any of aspects 22-27, further comprising a membrane including:
an oxidation zone, the oxidation zone comprising the metal oxide and configured to oxidize the at least one alkane having a carbon chain of five or more and the at least one alkane having a carbon chain of four or less;
a reduction zone, the reduction zone configured to reduce an oxygen-containing compound to anionic oxygen;
an electron barrier disposed between the oxidation zone and the reduction zone, the electron barrier being configured to allow transmission of the anionic oxygen from the reduction zone to the oxidation zone and to resist transmission of electrons from the oxidation zone to the reduction zone; and
a conductor attached to the oxidation zone and the reduction zone, the conductor configured to conduct electrons from the oxidation zone to the reduction zone.

Aspect 29. The system of any of aspects 22-28, wherein the gas hourly space velocity of the reactor is greater than 1,000 hr$^{-1}$ and less than 10,000 hr$^{-1}$.

Aspect 30. The system of any of aspects 22-29, wherein the gas hourly space velocity of the reactor is greater than 1,200 hr$^{-1}$ and less than 9,000 hr$^{-1}$.

BRIEF DESCRIPTION OF THE FIGURES

The invention is best understood from the following detailed description when read in connection with the accompanying drawings, with like elements having the same reference numerals. Included in the drawings are the following figures.

DETAILED DESCRIPTION OF THE INVENTION

The present inventors have discovered that particular methods, systems, and apparatuses may be employed to efficiently produce olefins by cracking hydrocarbon feeds comprising alkanes, and particularly two or more alkanes. Although steam cracking, the most common process for producing olefins, is generally endothermic, the inventors recognized that olefins can be exothermically produced from certain alkanes using particular metal oxides. Using the particular metal oxides, the inventors discovered that efficient methods of producing olefins from a hydrocarbon feed may be obtained by utilizing the heat/energy from an exothermic reaction of a first alkane to drive an endothermic reaction of a second alkane. For example, a first alkane may be cocracked with a second alkane of a different carbon chain length, such that the heat of reaction associated with the cracking of the first alkane to an olefin promotes the cracking of the second alkane to an olefin. Accordingly, using the thermodynamically efficient methods, oxidizing agents, and/or hydrocarbon feed streams discussed herein, desirable yields and selectivities for producing ethylene and propylene can be obtained at lower temperatures while producing lower amounts of undesirable byproducts, such as carbon dioxide ("$CO_2$") and carbon monoxide ("CO"). For example, the methods, systems, and apparatuses disclosed herein may advantageously enable reductions of up to 90% for $CO_2$ and almost complete elimination of nitric oxide ("NOx") emissions.

Figure 1:
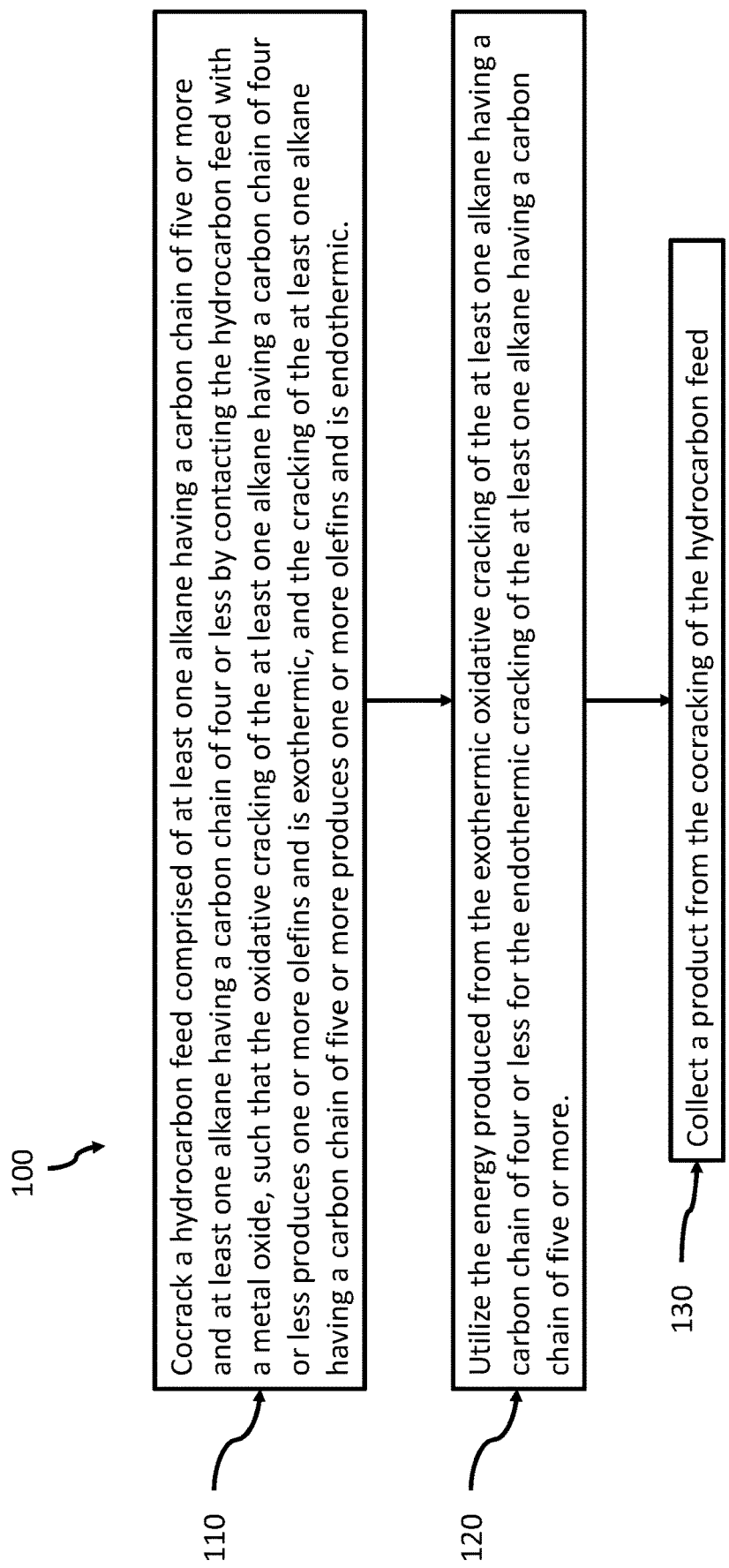
FIG. 1 illustrates a first embodiment of a method for producing one or more olefins by oxidative dehydrogenation cracking of a hydrocarbon feed in accordance with aspects of the invention.

FIG. 1 illustrates a non-limiting, exemplary embodiment of a method 100 for producing one or more olefins by oxidative dehydrogenation cracking of a hydrocarbon feed comprising at least one alkane. Cracking and/or cocracking of the hydrocarbon feed includes reaction mechanisms that produce products (e.g., olefins, alkenes, lower molecular weight alkanes, alkynes, etc.) having a lower number average molecular weight than the hydrocarbon feed. Cocracking two or more alkanes of a hydrocarbon feed includes cracking a first alkane concurrently with the cracking of at least a second alkane. The cocracking of the alkanes may occur in the same or in different reactors, which is discussed further below.

The hydrocarbon feed may be cracked or cocracked by oxidative dehydrogenation using an oxygen transfer agent comprising a metal oxide, as further discussed below. Oxidative dehydrogenation mechanisms occur according to the following generalized formula of Equation 1:

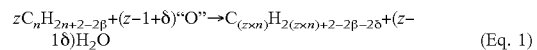

(Eq. 1)

where z=the number of reacting molecules; n=the number of carbon atoms in the reacting molecule; β=the degree of unsaturation where the value is zero for single bonds, one for double bonds and molecular rings, and two for triple bonds; and δ=the change in the degree of unsaturation. The metal oxide may be used in methods, systems, or apparatuses discussed herein as a catalyst, which promotes catalytic use of molecular oxygen, or as a reducible agent, which has been oxidized, to provide an oxygen atom to oxidize the alkanes of the hydrocarbon feed. A few examples of the reactions described by Equation 1, which may be promoted using a metal oxide or oxygen transfer agent according to the present invention, are shown in Table 1.

TABLE 1

| Starting Molecule, $C_nH_y$ | Number of starting molecules = z | $C_n$ Starting material | Degree unsaturation in starting molecule = β | Change of unsaturation in product = α | Moles of water | Moles of oxygen ($O_2$) | $C_n$ Product | $H_n$ Product | Product Formula | Product Name |
|---|---|---|---|---|---|---|---|---|---|---|
| $CH_4$ | 6 | 1 | 0 | 4 | 9 | 4.5 | 6 | 6 | $C_6H_6$ | Benzene |
| $C_3H_8$ | 2 | 3 | 0 | 1 | 2 | 1 | 6 | 12 | $C_6H_{12}$ | Hexene |
| $C_2H_6$ | 2 | 2 | 0 | 2 | 3 | 1.5 | 4 | 6 | $C_4H_6$ | Butyne |

TABLE 1-continued

| Starting Molecule, $C_nH_y$ | Number of starting molecules = z | $C_n$ Starting material | Degree unsaturation in starting molecule = β | Change of unsaturation in product = α | Moles of water | Moles of oxygen ($O_2$) | $C_n$ Product | $H_n$ Product | Product Formula | Product Name |
|---|---|---|---|---|---|---|---|---|---|---|
| $CH_4$ | 2 | 1 | 0 | 1 | 2 | 1 | 2 | 4 | $C_2H_4$ | Ethylene |
| $C_4H_8$ | 1 | 4 | 1 | 1 | 1 | 0.5 | 4 | 6 | $C_4H_6$ | Butyne |
| $C_3H_6$ | 2 | 3 | 1 | 2 | 3 | 1.5 | 6 | 8 | $C_6H_8$ | Cyclohexadiene |
| $CH_4$ | 2 | 1 | 0 | 0 | 1 | 0.5 | 2 | 6 | $CH_3CH_3$ | Ethane |
| $CH_3CH_3$ | 1 | 2 | 0 | 1 | 1 | 0.5 | 2 | 4 | $CH_2CH_2$ | Ethylene |

Using ethane as an example, the oxidative dehydrogenation cracking reaction to form olefins from ethane may either be conducted catalytically in the presence of molecular oxygen, as shown in Equation 2, $$C_2H_6 + \tfrac{1}{2}O_2 \rightarrow C_2H_4 + H_2O \quad (2)$$

or in a cyclic redox manner in the presence or absence of molecular oxygen, as shown in Equations 3-4.

$$C_2H_6 + MeO^{ox} \rightarrow C_2H_4 + H_2O + MeO^{red} \quad (3)$$

$$MeO^{red} + \tfrac{1}{2}O_2 \rightarrow MeO^{ox} \quad (4)$$

Preferably, in addition to the oxidative dehydrogenation cracking of saturated hydrocarbons to less saturated hydrocarbons, the oxygen transfer agents perform oxidative dehydrogenation cracking of hydrocarbons having a larger carbon chain (e.g., a higher molecular weight) to hydrocarbons having a shorter carbon chain (e.g., a lower molecular weight). As one example, Equations 5 and 6 show the oxidative dehydrogenation cracking reactions of hexane to ethylene.

$$C_6H_{14} + \tfrac{1}{2}O_2 \rightarrow 3C_2H_4 + H_2O \quad (5)$$

$$C_6H_{14} + MeO^{ox} \rightarrow 3C_2H_4 + H_2O + MeO^{red} \quad (6)$$

Figure 4:
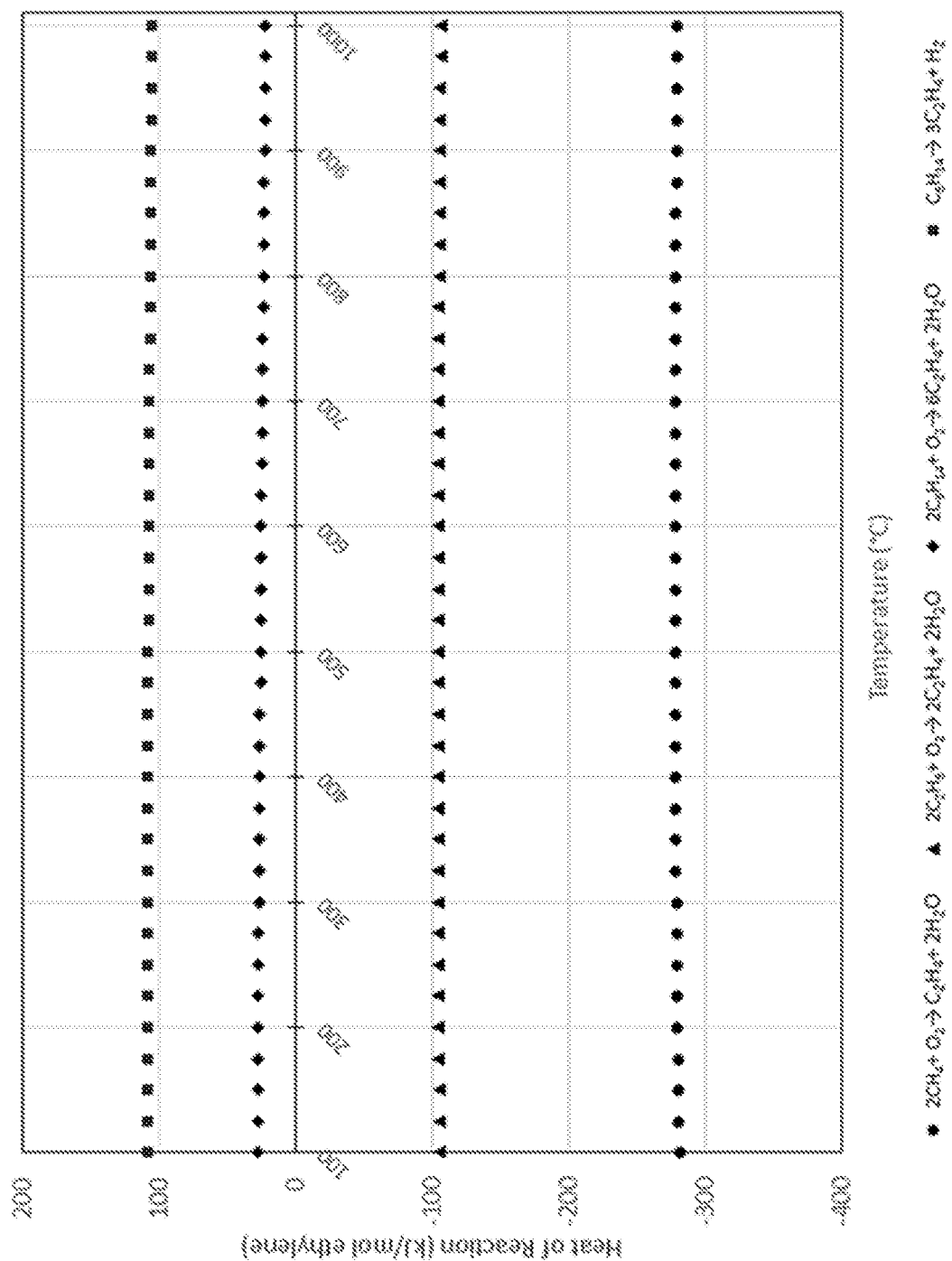
FIG. 4 is a graph illustrating the amount of energy produced or required for cracking certain alkanes according to aspects of the invention.

In step 110, a hydrocarbon feed comprised of at least one alkane having a carbon chain of five or more and at least one alkane having a carbon chain of four or less is cocracked by contacting the hydrocarbon feed with a metal oxide. Cracking of the at least one alkane having a carbon chain of four or less by oxidative dehydrogenation using a metal oxide to produce one or more olefins is exothermic. Cracking of the at least one alkane having a carbon chain of five or more by oxidative dehydrogenation using a metal oxide to produce one or more olefins is endothermic. Water may be produced as a byproduct of the cracking of the at least one alkane having a carbon chain of four or less and/or the at least one alkane having a carbon chain of five or more. For example, FIG. 4 illustrates that the cracking of alkanes may or may not produce water as a byproduct.

The metal oxide is configured to crack a hydrocarbon feed comprising alkanes by way of oxidative dehydrogenation (also referred herein as oxidative dehydrogenation cracking or cocracking). The metal oxide may comprise part of or all of an oxygen transfer agent. The oxygen transfer agent comprising a metal oxide may be configured for oxidative dehydrogenation cocracking of a first alkane having a carbon chain of five or more and a second alkane having a carbon chain of four or less. Additionally and/or alternatively, the metal oxides disclosed herein may be used for oxidative coupling of methane in addition to the oxidative dehydrogenation mechanisms associated with the cracking of a hydrocarbon feed.

The metal oxide comprises oxygen and at least one metal, preferably at least one element selected from the group consisting of lanthanum ("La"), cerium ("Ce"), praseodymium ("Pr"), terbium ("Tb"), neodymium ("Nd"), and dysprosium ("Dy"). The oxides may be used as commonly mined mixtures, such as didymium. Preferably, the metal oxide comprises Pr and any compounds, complexes, composites, or the like thereof. The oxygen transfer agent may be comprised of at least 0.5% by weight metal oxide(s) and up to 100% by weight metal oxide(s). For example, the oxygen transfer agent may comprise an amount, by weight, of metal oxide ranging from 5% to 95%; preferably 15% to 90%; more preferably 20% to 85%; more preferably 25% to 80%; more preferably 30% to 75%; more preferably 35% to 70%; and/or more preferably 40% to 65%. Additionally and/or alternatively, the oxygen transfer agent may comprise an amount of metal oxide, by weight, ranging from 0.5% to 10%; 10% to 20%; 20% to 30%; 30% to 40%; 40% to 50%; 50% to 60%; 60% to 70%; 70% to 80%; 80% to 90%; or 90% to 100%. Mixtures of different metal oxides may also be utilized. The oxygen transfer agent may include at least one promoter integrally dispersed (e.g., uniformly dispersed) with the metal oxide. In one embodiment, the promoter is selected from the group consisting of sodium ("Na"), lithium ("Li"), calcium ("Ca"), magnesium ("Mg"), strontium ("Sr"), and barium ("Ba").

The oxygen transfer agent may also comprise a zeolite that may be configured to accelerate the rate of oxidative dehydrogenation cracking of the hydrocarbon feed. Preferably, the zeolite has a composition in accordance with the general formula: $M_{2/n}O \cdot Al_2O_3 \cdot ySiO_2 \cdot wH_2O$ where y is from 2 to 1,000,000,000, M is a positively charged element for balancing the charge of the zeolite and may include protons, alkaline metals, alkaline earth metals or other elements known to those skilled in the art, n represents the cation valence and w represents the number of water molecules per zeolite unit structure, such that, at least 5% of n are protons. For example, the zeolite may have a composition in accordance with the above general formula where y is from 4 to 35. In one embodiment, the zeolite comprises ZSM-5, while in another embodiment the zeolite is selected from a group consisting of ZSM-5, MCM 22, and MCM 56. Suitable amounts of Bronsted and/or Lewis acids may be utilized to optimize the activity of the zeolites. The molar ratio of the amount of metal oxide(s) to zeolite(s) may range from, e.g., 100:1 to 1:100; 95:5 to 5:95; 90:10 to 10:90; 85:15 to 15:85; 80:20 to 20:80; 75:25 to 25:75; 70:30 to 30:70; 65:35 to 35:65; 60:40 to 40:60; and/or 55:45 to 45:55. Additionally and/or alternatively, the molar ratio of the amount of metal oxide(s) to zeolite(s) may range from ranging from 95:5 to 90:10; 90:10 to 85:15; 85:15 to 80:20; 80:20 to 75:25; 75:25 to 70:30; 70:30 to 65:35; 65:35 to 60:40; 60:40 to 55:45; 55:45 to 50:50; 50:50 to 45:55; 45:55 to 40:60; 40:60 to 35:65; 35:65 to 30:70; 30:70 to 25:75; 25:75 to 20:80; 20:80 to 15:85; 15:85 to 10:90; or 10:90 to 5:95.

The oxygen transfer agents disclosed herein may be prepared by any methods known by those skilled in the art, including, but not limited to, precipitation, co-precipitation, impregnation, granulation, spray drying, dry mixing, etc. Precursors may be transformed into active agents by calcination at temperatures suitable for the formation of the active components, e.g., in the range of 400° to 1,100° C. The calcination may be performed under any atmosphere, such as air, inert gases, hydrogen, carbon monoxide, and hydrocarbon gases, so as to form the active oxygen transfer agents of the present invention. The oxygen transfer agent may be admixed or otherwise formulated with binders, supports, carriers and the like using any conventional procedures known in the art and may be utilized in any suitable shape or physical form such as powder, granules, pellets, beads, rings, monoliths, extrudates and the like. Suitable oxygen transfer agents and methods of manufacturing the same may be found in PCT Patent Application no. PCT/US17/39448, which is incorporated herein in its entirety for all purposes.

The hydrocarbon feed may, for example, include one or more aliphatic hydrocarbons (alkanes), such as methane, ethane, propane, butane, hexane, heptane, octane, etc. Substances other than alkanes may also be present in the hydrocarbon feed. Preferably, the hydrocarbon feed includes at least one alkane having a carbon chain of five or more and at least one alkane having a carbon chain of four of less. The hydrocarbon feed may be derived from natural gas obtained from unconventional well drilling techniques and/or crude oil or gas obtained from traditional well drilling techniques. In one embodiment, the hydrocarbon feed includes alkanes obtained from natural gas as well as alkanes from oil and/or gas obtained from traditional well drilling techniques. It is also contemplated herein that one or more alkanes of the hydrocarbon feed stream may be derived from a renewable resource, such as algae, plant materials, etc.

In step 120, the energy produced from the exothermic cracking of the alkane having a carbon chain of four or less is utilized for the endothermic cracking of the at least one alkane having a carbon chain of five or more. As shown in Table 2, using oxygen transfer agents and/or metal oxides disclosed herein, oxidative dehydrogenation cracking of alkanes having a carbon chain of four or less is exothermic, while oxidative dehydrogenation cracking of alkanes having a carbon chain of five or more is endothermic.

TABLE 2

| Oxidative Dehydrogenation Reactions | | | | | Feed ΔH°/mol |
|---|---|---|---|---|---|
| $CH_4$ | $0.5O_2$ | = | $0.5C_2H_4$ | $H_2O$ | −141.008 |
| $C_2H_6$ | $0.5O_2$ | = | $C_2H_4$ | $H_2O$ | −114.856 |
| $C_3H_8$ | $0.5O_2$ | = | $1.5C_2H_4$ | $H_2O$ | −59.528 |
| $C_4H_{10}$ | $0.5O_2$ | = | $2C_2H_4$ | $H_2O$ | −11.498 |
| $C_5H_{12}$ | $0.5O_2$ | = | $2.5C_2H_4$ | $H_2O$ | 35.792 |
| $C_6H_{14}$ | $0.5O_2$ | = | $3C_2H_4$ | $H_2O$ | 81.934 |
| $C_7H_{16}$ | $0.5O_2$ | = | $3.5C_2H_4$ | $H_2O$ | 128.704 |
| $C_8H_{18}$ | $0.5O_2$ | = | $4C_2H_4$ | $H_2O$ | 175.706 |

The hydrocarbon feed may comprise a select composition of alkanes to improve the yield of olefin, the selectivity of desired olefins, and/or to reduce undesired by products. For example, the hydrocarbon feed may have a composition of alkanes having a carbon chain of four or less that includes one or more of methane, ethane, propane, and/or butane. Preferably, the alkane having a carbon chain of four or less consists of methane, ethane, and/or propane. The composition of alkanes having a carbon chain of five or more may comprise naphtha—including light naphtha (i.e., a naphtha composition having predominantly alkanes with a carbon chain of 5-6 and a boiling point at atmospheric pressure of about 30° C. to 90° C.) and/or heavy naphtha (i.e., a naphtha composition having predominantly alkanes with a carbon chain of 6-12 and a boiling point at atmospheric pressure of about 90° C. to about 200° C.).

The hydrocarbon feed may have a composition with a molar ratio of alkanes having a carbon chain of four or less to alkanes having a carbon chain of five or more of 1:10 to 10:1; preferably 2:10 to 10:5; more preferably 2:10 to 10:8; more preferably 2:10 to 10:10; more preferably 3:10 to 9:10; more preferably 3:10 to 8:10; more preferably 3:10 to 7:10; more preferably 3:10 to 6:10; more preferably 3:10 to 6:10; more preferably 3:10 to 5:10; or more preferably 3:10 to 4:10. The composition of the hydrocarbon feed may be configured such that the energy theoretically produced from the exothermic oxidative dehydrogenation of the at least one alkane having a carbon chain of four or less ranges from 0% to 10% greater than the energy theoretically required for the endothermic cracking of the at least one alkane having a carbon chain of five or more. The theoretical amount of energy required for the endothermic and/or exothermic oxidative dehydrogenation cracking of the at least one alkane can be determined by calculating the amount of energy required for oxidative dehydrogenation cracking of the alkane to ethylene without any byproducts or wasted energy, e.g., using the tables provided herein and/or FIGS. 3 and 4. In one embodiment, the energy theoretically produced by the exothermic oxidative dehydrogenation cracking is greater than the energy theoretically required by the endothermic oxidative dehydrogenation cracking by 0% to 90%, e.g., preferably 0% to 80%; more preferably 0% to 70%; more preferably 0% to 60%; more preferably 0% to 50%; more preferably 0% to 40%; more preferably 0% to 30%; or more preferably 0% to 20%. Although it may be preferable in certain circumstances to configure method 100 such that the energy produced by the exothermic oxidative dehydrogenation cracking is net neutral to the energy utilized by the endothermic oxidative dehydrogenation cracking, method 100 may be configured to produce an amount of energy from the exothermic oxidative dehydrogenation cracking that is greater than the energy utilized by the endothermic oxidative dehydrogenation cracking by 10% or more, preferably 20% or more, 40% or more, 60% or more, 80% or more, 100% or more, or 150% or more. The energy produced by exothermic oxidative dehydrogenation cracking, in excess of the energy utilized by the endothermic oxidative dehydrogenation cracking, may be used for other manufacturing processes, such as heating feed streams, producing steam, etc.

Figure 3:
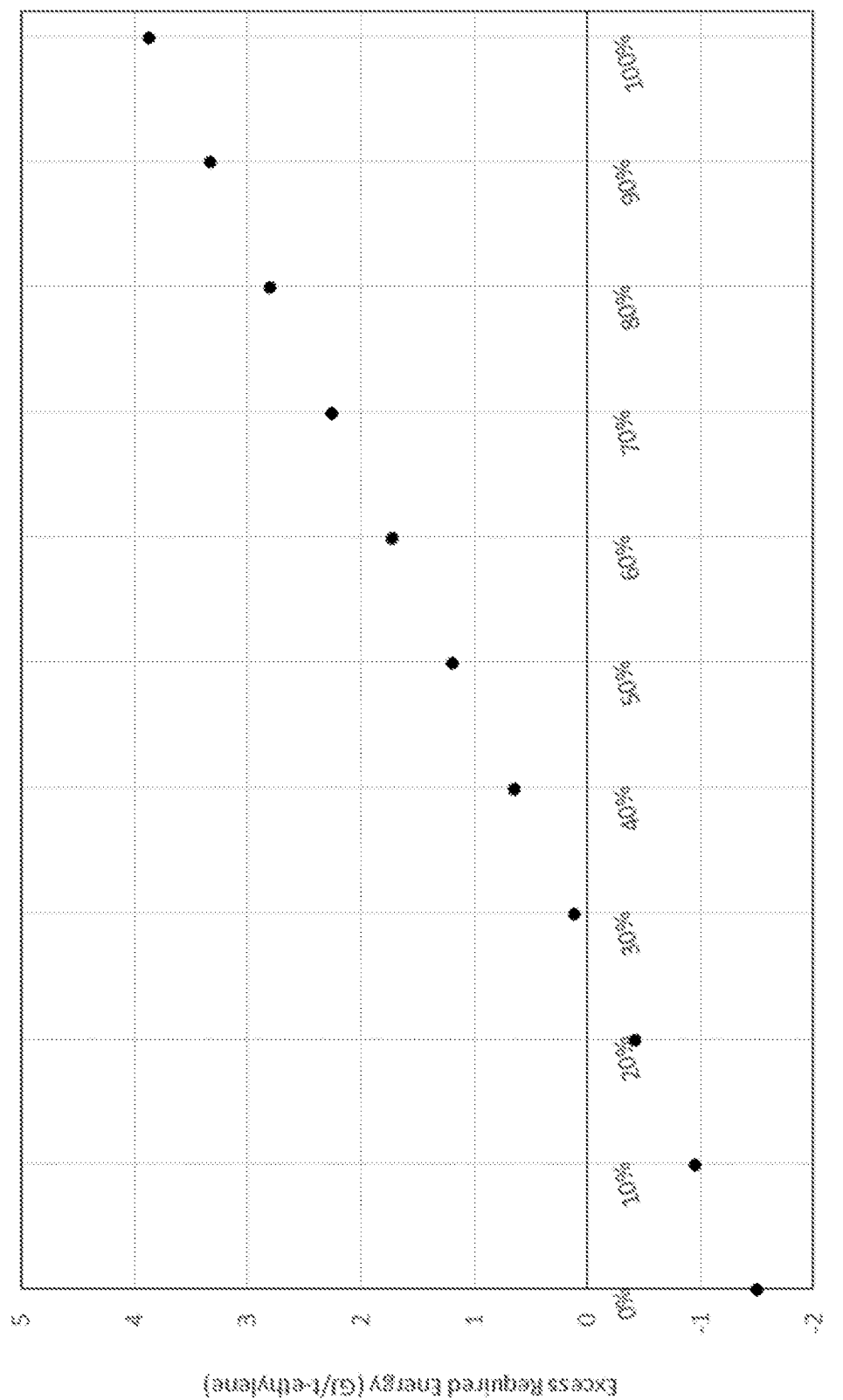
FIG. 3 is a graph illustrating the amount of energy produced or required for oxidative dehydrogenation cocracking a hydrocarbon feed comprising ethane and naphtha in accordance with aspects of the invention.

According to one aspect, the hydrocarbon feed includes at least one alkane having a carbon chain of four or less comprising ethane and at least one alkane having a carbon chain of five or more comprising naphtha (e.g., light and/or heavy naphtha). FIG. 3 is a graph illustrating the amount of energy produced or required for oxidative dehydrogenation cocracking a hydrocarbon feed comprising ethane and naphtha in accordance with embodiment of the invention. The hydrocarbon feed may have a composition with a molar ratio of ethane to naphtha that ranges from 3:10 to 9:10; preferably 3:10 to 8:10; more preferably 3:10 to 7:10; more preferably 3:10 to 6:10; more preferably 3:10 to 6:10; more preferably 3:10 to 5:10; or more preferably 3:10 to 4:10. Table 3, shown below, provides information regarding the oxidative dehydrogenation cracking of ethane and naphtha.

TABLE 3

| Reaction | | Heat of Formation (kJ/mol $C_2H_4$) at T = 650° C. | Ratio of Reaction to Hexane Oxidation to Achieve Heat Neutrality |
|---|---|---|---|
| Hexane Cracking | $C_6H_{14} \rightarrow 3C_2H_4 + H_2$ | +107.06 | — |
| Hexane Oxidation | $2C_6H_{14} + O_2 \rightarrow 6C_2H_4 + 2H_2O$ | +24.55 | — |
| Ethane Oxidation | $2C_2H_6 + O_2 \rightarrow 2C_2H_4 + 2H_2O$ | −104.42 | 0.24 |
| Methane Oxidation | $2CH_4 + O_2 \rightarrow C_2H_4 + 2H_2O$ | −278.55 | 0.09 |

By utilizing the energy from the exothermic cracking of the at least one alkane having a carbon chain of four or less to promote the endothermic cracking of the at least one alkane having a carbon chain of five or more, method 100 may produce olefins at a higher yield, a lower temperature, and/or with significantly reduced undesired byproducts (e.g., CO, $CO_2$, $NO_x$, etc.). For example, cocracking of the hydrocarbon feed may produce a product having a composition comprising at least 50% by weight of ethylene, propylene, or a combination thereof, while being performed at a temperature of greater than 500° C. and less than 1000° C. In one embodiment, cocracking of the hydrocarbon feed is performed at a temperature of greater than 600° C. and less than 850° C. and produces a product having a composition comprising at least 40% by weight of ethylene, propylene, or a combination thereof. In another embodiment, cocracking of the hydrocarbon feed is performed at a temperature of greater than 600° C. and less than 850° C. and produces a product having a composition comprising at least 65% by weight of olefins. In yet a further embodiment, cocracking of the hydrocarbon feed is performed at a temperature of greater than 600° C. and less than 750° C. and produces a product having a composition comprising at least 65%, by weight, of olefins. As mentioned above, improved olefin yield at lower cracking or cocracking temperatures may be obtained using the disclosures provided herein, e.g., as illustrated below in Table 4.

TABLE 4

|  | Ethane | Naphtha |
|---|---|---|
| Total Energy Required, GJ/t ethylene | 17-21 | 26-31 |
| Energy % for pyrolysis | 23% | 73% |
| Pyrolysis energy, GJ/t ethylene (avg.) | 4.37 | 20.805 |
| Wt. % Ethylene product (avg.) | 82% | 30% |
| Energy use per ton feed conversion | 3.58 | 6.24 |
| Hydrogen yield, wt % | 4% | 1% |
| Heat available from hydrogen, GJ/t-ethylene | 7.45 | 4.73 |
| Energy Excess (Deficit), GJ/t-ethylene | 3.86 | −1.51 |

In step 130, the product from the cocracking of the hydrocarbon feed is collected. The product may be collected by any suitable means known to one of ordinary skill in art. As mentioned above, the product may comprise one or more olefins and water as a byproduct. Preferably, the product from the cocracking of the hydrocarbon feed comprises olefins at 30% or more, preferably 35% or more, preferably 38% or more, preferably 40% or more, preferably 43% or more, preferably 45% or more, preferably 48% or more, preferably 50% or more, preferably 52% or more, preferably 55% or more, preferably 58% or more, preferably 60% or more, preferably 62% or more, preferably 64% or more, preferably 66% or more, preferably 68% or more, or preferably 70% or more, by weight. The composition of the olefins may include ethylene, propylene, or a combination thereof in an amount of 30% or more, preferably 33% or more, preferably 35% or more, preferably 38% or more, preferably 40% or more, preferably 43% or more, preferably 45% or more, preferably 48% or more, preferably 50% or more, preferably 52% or more, preferably 55% or more, preferably 58% or more, preferably 60% or more, preferably 62% or more, preferably 64% or more, preferably 66% or more, preferably 68% or more, preferably 70%, preferably 72% or more, preferably 74% or more, preferably 76% or more, preferably 78% or more, preferably 80% or more, preferably 82% or more, preferably 84% or more, preferably 86% or more, or preferably 88% or more, by weight.

The product collected in step 230 may be further fractionated, purified, recycled, converted, etc. For example, the product may purified downstream in order to isolate polymer grade olefins. For example, ethylene fractionation may include one or more driers in order to remove water prior to feeding the dried product to a distillation column. The polymer grade olefins may then be sold as raw materials for the production of higher molecular weight products by oligomerization. Numerous catalysts and processes are known for the oligomerization of olefins generally, and of ethylene particularly, all of which may be employed for converting the polymer grade olefins made according to the various methods of the present invention to higher molecular weight products. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like. Higher hydrocarbon products of interest may include aviation fuels, kerosene, or intermediate refining streams. Examples of suitable catalysts for oligomerization of olefins may be found in PCT Publication no. WO 2016/049144, which is incorporated herein in its entirety for all purposes.

Figure 2:
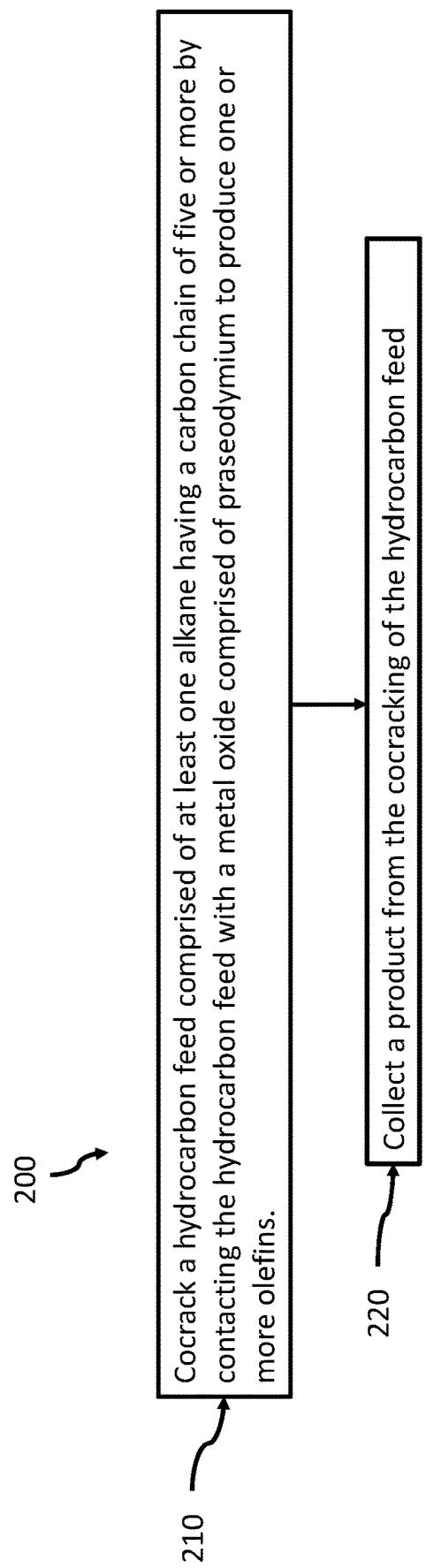
FIG. 2 illustrates a second embodiment of a method for producing one or more olefins by oxidative dehydrogenation cracking of a hydrocarbon feed according to aspects of the invention.

FIG. 2 illustrates a non-limiting, exemplary embodiment of a method 200 for producing one or more olefins by oxidative dehydrogenation cracking of a hydrocarbon feed comprising at least one alkane.

In step 210, a hydrocarbon feed comprised of at least one alkane having a carbon chain of five or more is cracked by oxidative dehydrogenation cracking by contacting the hydrocarbon feed with a metal oxide comprised of praseodymium to produce one or more olefins. Although step 210 is illustrated in FIG. 2 as oxidative dehydrogenation cracking of at least one alkane having a carbon chain of five or more, in one embodiment of method 200 at least one alkane having a carbon chain of four or less is cracked by oxidative dehydrogenation cracking concurrently with (e.g., cocracked with) the at least one alkane having a carbon chain of five or more. In another embodiment, however, the hydrocarbon feed of method 200 predominately includes or consists of alkanes having a carbon chain of five or more. Method 200 may employ metal oxides, and oxygen transfer agents more generally, similar to or the same as those discussed herein with respect to other embodiments of the invention.

In step 220, the product from the cracking of the hydrocarbon feed is collected. The product may have a composition similar to product of method 100 and may be collected by any suitable means known to one of ordinary skill in art.

Figure 5:
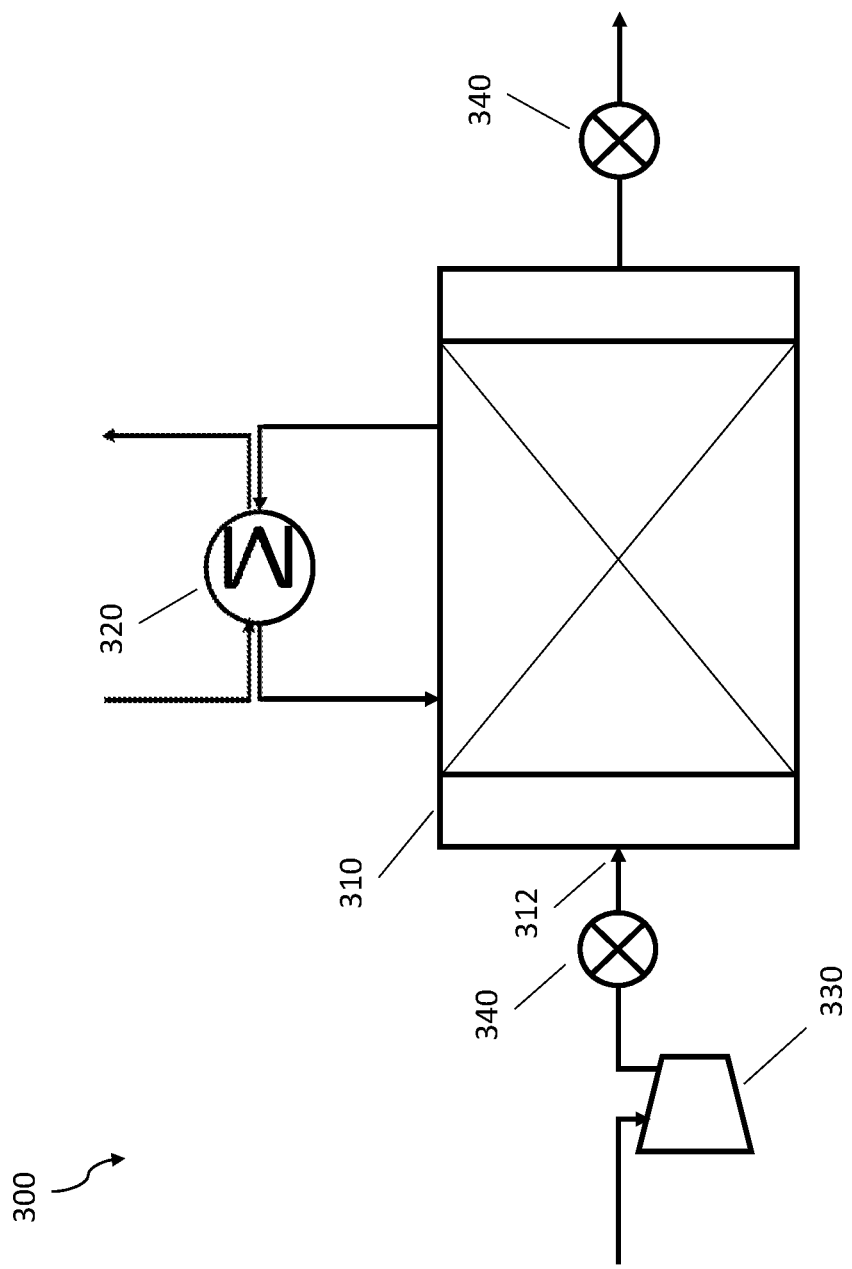
FIG. 5 is a schematic of a system for cracking or cocracking of a hydrocarbon feed in accordance with aspects of the invention.

FIG. 5 is a schematic of an exemplary, non-limiting system 300 for cocracking of a hydrocarbon feed comprised of two or more alkanes. System 300 includes a reactor 310 containing an oxygen transfer agent and/or a metal oxide useful for the oxidative dehydrogenation cracking of hydrocarbons, as described above. System 300 may include any reactor type known to be useful for cracking hydrocarbons, and particularly reactors suitable for oxidative dehydrogenation cracking of hydrocarbons. Reactor 310 includes at least one inlet 312 configured for supplying at least one hydrocarbon feed stream to reactor 310 and at least one outlet configured to receive a product stream. The metal oxide may be comprised of praseodymium and configured for cocracking at least one alkane having a carbon chain of five or more and/or at least one alkane having a carbon chain of four or less by oxidative dehydrogenation cracking to produce one or more olefins. In one embodiment, the gas hour space velocity of the reactor is greater than 1,000 hr$^{-1}$ and less than 10,000 hr$^{-1}$. In another embodiment, the gas hour space velocity of the reactor is greater than 1,200 hr$^{-1}$ and less than 9,000 hr$^{-1}$.

As illustrated in FIG. 5, system 300 may include a heat exchanger 320 configured to add heat/energy to reactor 310 for promoting oxidative dehydrogenation cracking or to remove heat/energy produced by oxidative dehydrogenation cracking for other productive manufacturing uses. In one embodiment, however, system 300 is configured such that cocracking of at least one alkane having a carbon chain of four or less with at least one alkane having a carbon chain of five or more is energy net-neutral such that the energy produced does not require a heat exchanger to remove excessive heat/energy production. Accordingly, in one embodiment, system 300 does not include a heat exchanger or cooling jacket. System 300 may also include any number of suitable compressors/pumps 330 and valves 340.

Figure 6:
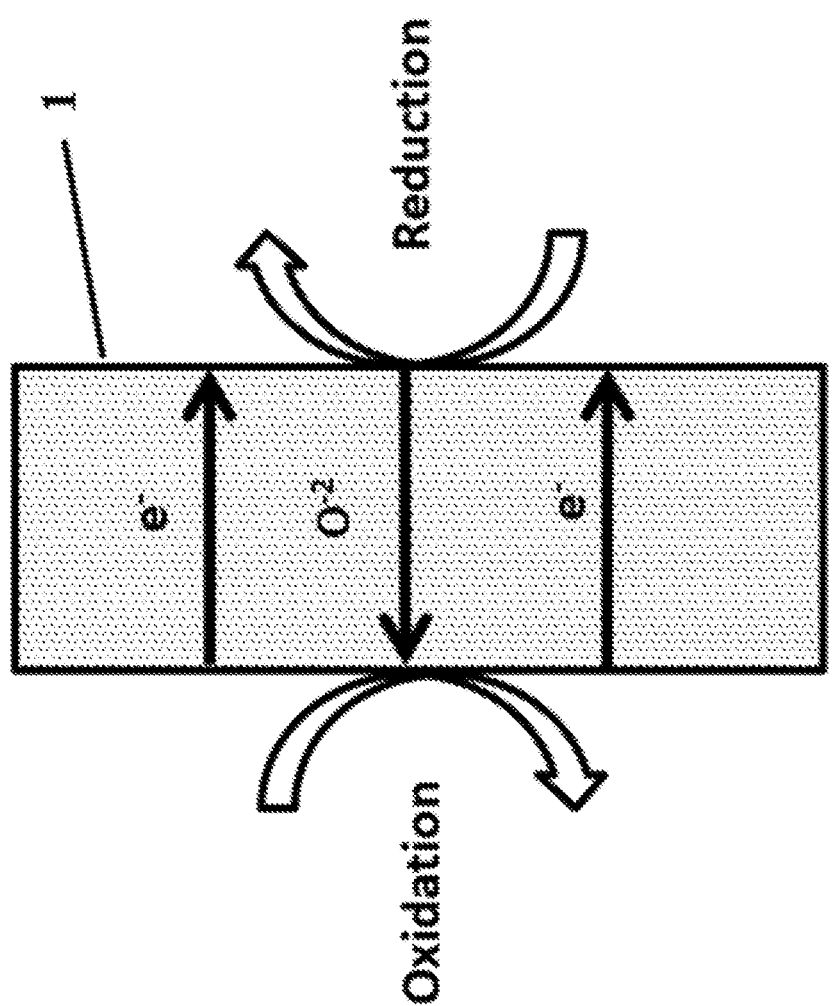
FIG. 6 is a first simplified schematic block diagram of a reactor according to aspects of the invention.
Figure 7:
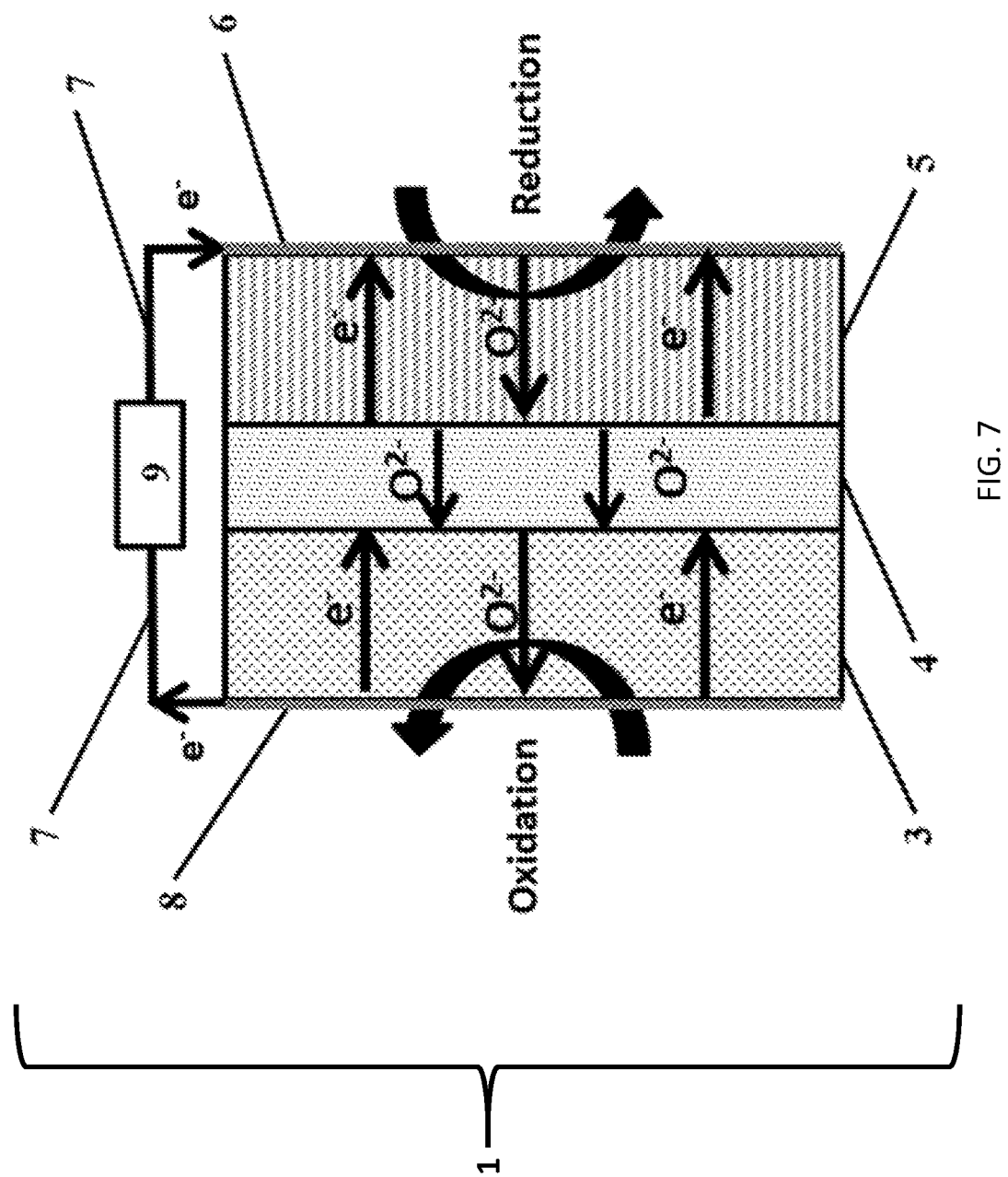
FIG. 7 is a second simplified schematic block diagram of a reactor in accordance with aspects of the invention.

FIGS. 6 and 7 are simplified schematic block diagrams of two electro-generative reactors 1 according to aspects of the invention. An electro-generative reactor utilizes favorable thermodynamics and kinetic factors in an electrochemical cell to generate byproduct electricity while bringing about a desired reaction. In one embodiment, the electro-generative reactor is a fuel cell that produces olefins and electricity. The amount of electricity produced may be optimized by varying the production ratio of products, such as olefins, water, $CO_2$, electricity, etc. Reactor 1 of FIG. 7 includes an oxidation zone 3, a reduction zone 5, an electron barrier 4 disposed between oxidation zone 3 and reduction zone 5, and a conductor 7 attached to oxidation zone 3 and reduction zone 5. The oxidation zone 3 includes an oxygen transfer agent and/or metal oxide. The oxidation zone 3 is configured to oxidize the at least one alkane having a carbon chain of five or more and the at least one alkane having a carbon chain of four or less. Preferably, the oxidation zone 3 is configured for oxidative dehydrogenation cocracking of at least one alkane having a carbon chain of five or more and at least one alkane having a carbon chain of four or less. The oxidation zone 3 may be comprised of mixed conductive materials, thereby conducting both oxygen anions and also having electronic conductivity. The reduction zone 5 is configured to reduce an oxygen-containing compound to anionic oxygen. The electron barrier 4 may be configured to allow transmission of the anionic oxygen from reduction zone 5 to oxidation zone 3 and to resist transmission of electrons from the oxidation zone 3 to the reduction zone 5. Conductor 7 is configured to conduct electrons from the oxidation zone 3 to the reduction zone 5. Suitable examples of electro-generative reactors and fuel cells may be found in U.S. Patent Publication no. 2017/0247803, which is incorporated herein in its entirety for all purposes.

Additionally and/or alternatively, in the embodiment depicted in FIG. 7, power 9 may be applied through conductor 7 to a reduction zone 5, which promotes the reduction of oxygen to oxygen anion in the cathode plate 6. However, in one embodiment, power is removed from the electro-generative fuel cell by way of conductor 7. The oxidation of the hydrocarbon feed stream occurs in the oxidation zone 3 and electrons are conducted through an anode plate 8 to complete the power circuit. Oxygen anions move through the electron barrier 4, which is intimately associated with the selective oxygen transfer agent and/or metal oxide in the oxidation zone 3. In this oxygen pumping embodiment, the effective pressure differential of oxygen between the reduction membrane and oxidation membrane is increased, thereby increasing the rate of oxygen anion transfer through the electron barrier.

Figure 8:
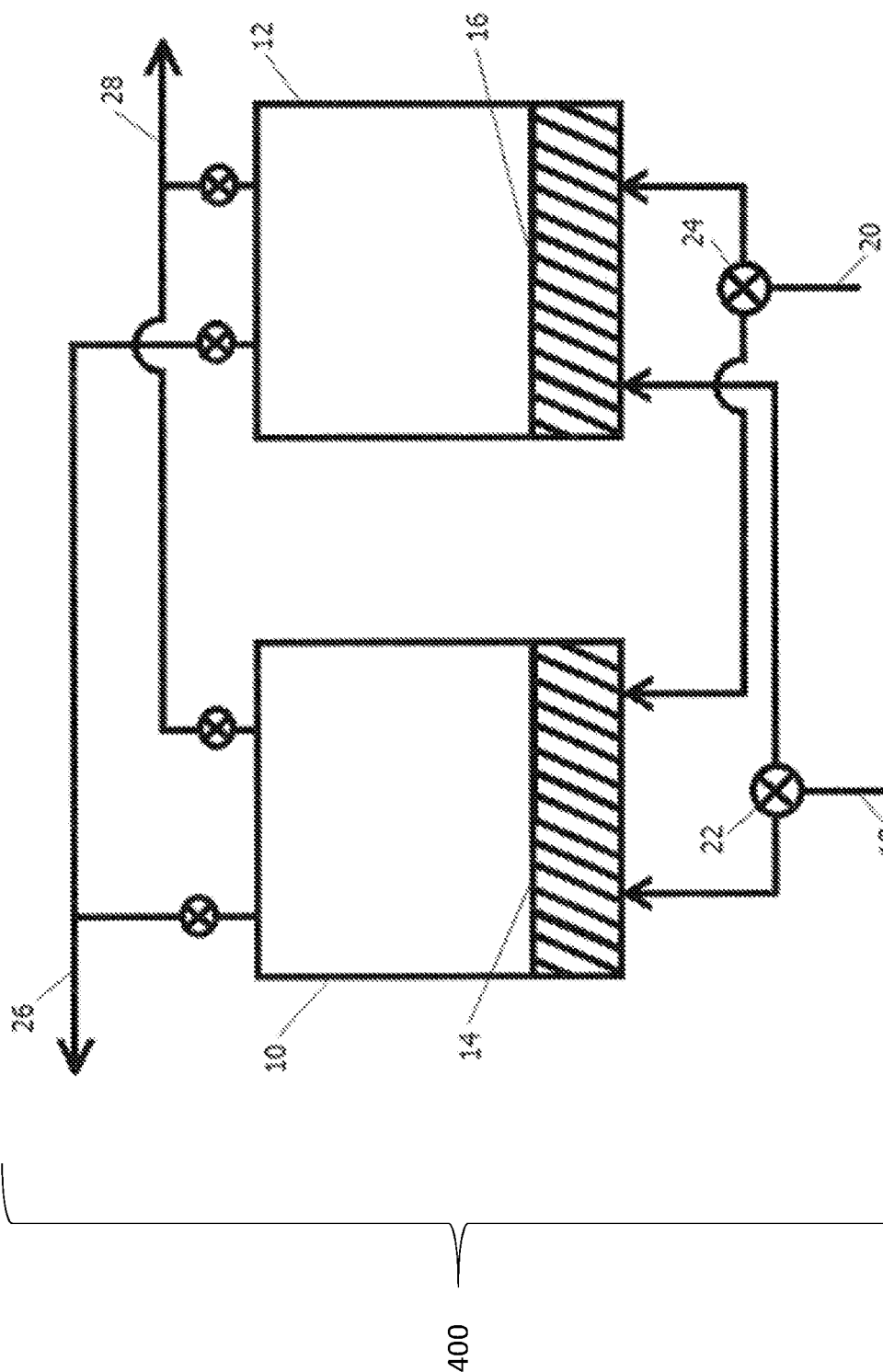
FIG. 8 illustrates a schematic of an embodiment of a system comprising two fixed-bed reactors configured for cracking or cocracking of a hydrocarbon feed according to aspects of the invention.

FIG. 8 illustrates a schematic of a non-limiting, exemplary system 400 comprising two fixed-bed reactors 10, 12. In the case of fixed bed reactors, multiple reactors may be used such that oxidative dehydrogenation cracking or cocracking and the re-oxidation of the oxygen transfer agent and/or metal oxide are occurring continuously as feed and air are alternately cycled to multiple reactors, such as the system illustrated in FIG. 8. The two fixed-bed reactors 10, 12 may each contain a layer of oxygen transfer agent 14, 16. A hydrocarbon feed line 18 for delivering a hydrocarbon feed, such as ethane for example, may include a valve 22 to selectively direct the hydrocarbon feed to either the first reactor 10 or the second reactor 12. If the first reactor 10 is selected, the hydrocarbon will pass through the layer of oxygen transfer agent 14, which promotes an oxidative dehydrogenation reaction, resulting in a product stream containing an unsaturated hydrocarbon, such as ethylene, and water that exits the first effluent line 26. During this process in the first reactor 10, the oxygen transfer agent 14 is reduced over time. In order to regenerate the agent, the feed stream is diverted through valve 22 to the second fixed bed reactor 12, and an oxygen-containing gas stream, such as air, from feed line 20 is fed through valve 24 to the first reactor 10. The oxygen-containing gas oxidizes the oxygen transfer agent 14, and the oxygen-depleted product gas exits effluent stream 28. As the oxygen transfer agent 14 in the first reactor 10 is being regenerated through oxidation, the second reactor 12 is producing one or more olefins and, optionally, byproduct water that exits effluent stream 26. Upon reaching the point where regeneration of the oxygen transfer agent 16 in the second reactor 12 is desired, the hydrocarbon feed and oxygen containing gas feeds may be switched using the valves 22, 24. This arrangement provides a continuous production of unsaturated hydrocarbon, as well as continuous oxygen transfer agent regeneration. Suitable examples of fixed bed reactors and fluid bed reactors may be found in PCT Patent Publication no. WO 2016/049144, which is incorporated herein in its entirety for all purposes.

Figure 9:
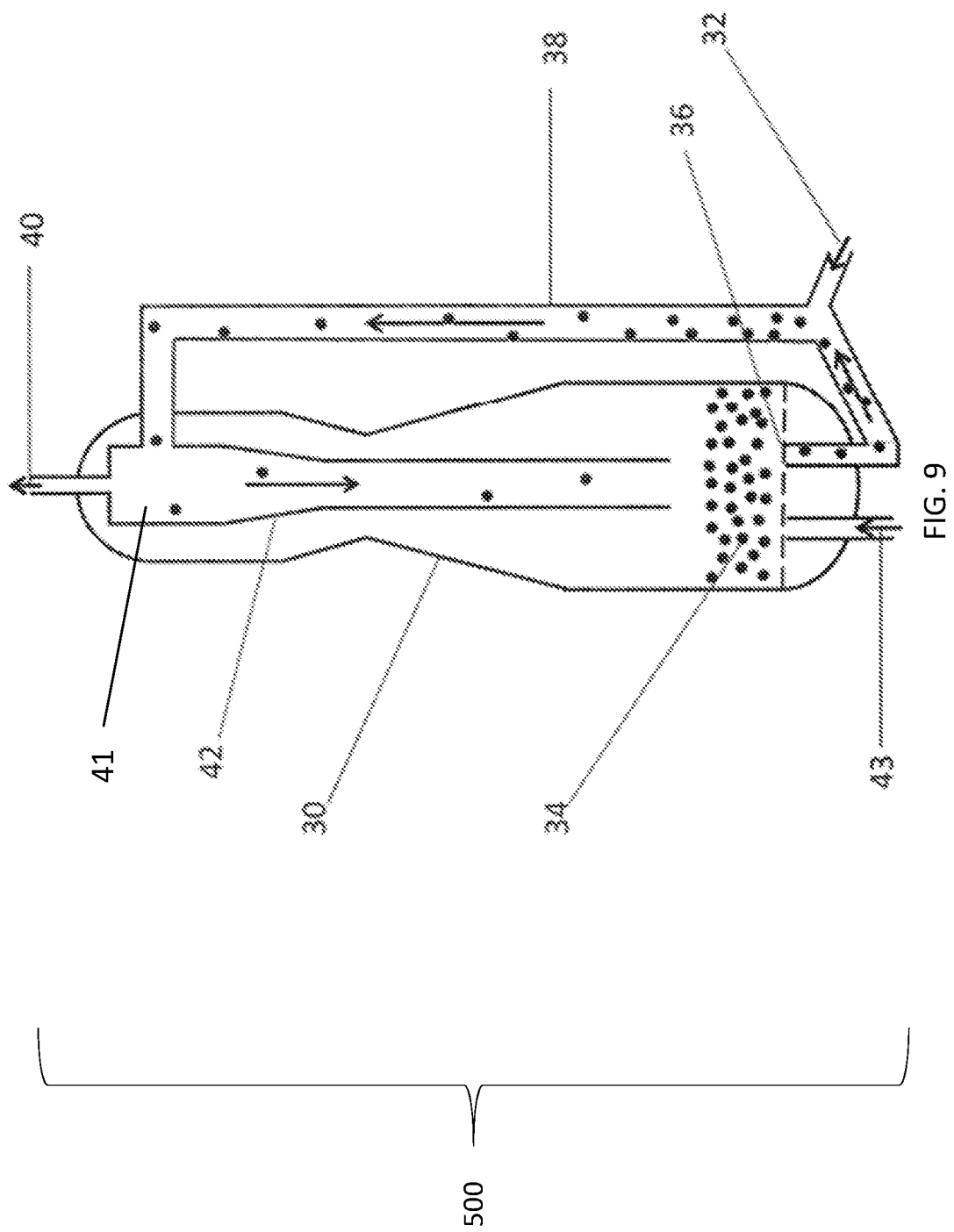
FIG. 9 illustrates a schematic of an embodiment of a system comprising a fluid bed reactor having a single riser for cracking or cocracking of a hydrocarbon feed in accordance with aspects of the invention.

FIG. 9 illustrates a schematic of a non-limiting, exemplary system 500 comprising a fluid bed reactor 30 and at least one cyclone system 41. The reactor of system 500 may consist of a single riser, whereby alkanes having a carbon chain of five or more are concurrently cracked (e.g., cocracked) with alkanes having a carbon chain of four or less. Although system 500 is illustrated in FIG. 9 as having a single riser, system 500 may be configured to have two or more risers (See, e.g., FIG. 10). System 500 includes a hydrocarbon feed stream 32, such as ethane, that is fed to the hydrocarbon reaction section 38 of reactor 30. Also fed to the hydrocarbon reaction section 38 of reactor 30 is an oxygen transfer agent and/or metal oxide from bed 34 through an outlet 36 underneath the bed 34. The hydrocarbon feed and the oxygen transfer agent and/or metal oxide travel together vertically upwards through the height of the reaction section 38. Although the hydrocarbon feed and oxygen transfer agent travel vertically through the reaction section in FIG. 9, in other embodiments of the invention, the metal oxide(s) flow vertically downwards and the hydrocarbon feed flows counter-currently downwards or co-currently upwards. As would be understood by those of skill in the art, the flow rate of reactants and dimensions of the reaction zone 38 may be optimized to maximize the reaction rate for the production of unsaturated hydrocarbons, such as ethylene. The reduced oxygen transfer agent and/or metal oxide may then returned to the bed 34 via an internal return line 42, while the unsaturated hydrocarbon product exits reactor 30 via an outlet 40. In order to regenerate the oxygen transfer agent, an oxygen-containing gas, such as air, is fed through a second inlet 43 to the bottom of the bed 34. Any oxygen-depleted gas exiting the top of the bed 34 may also exit through the outlet 40 with the product effluent.

Figure 10:
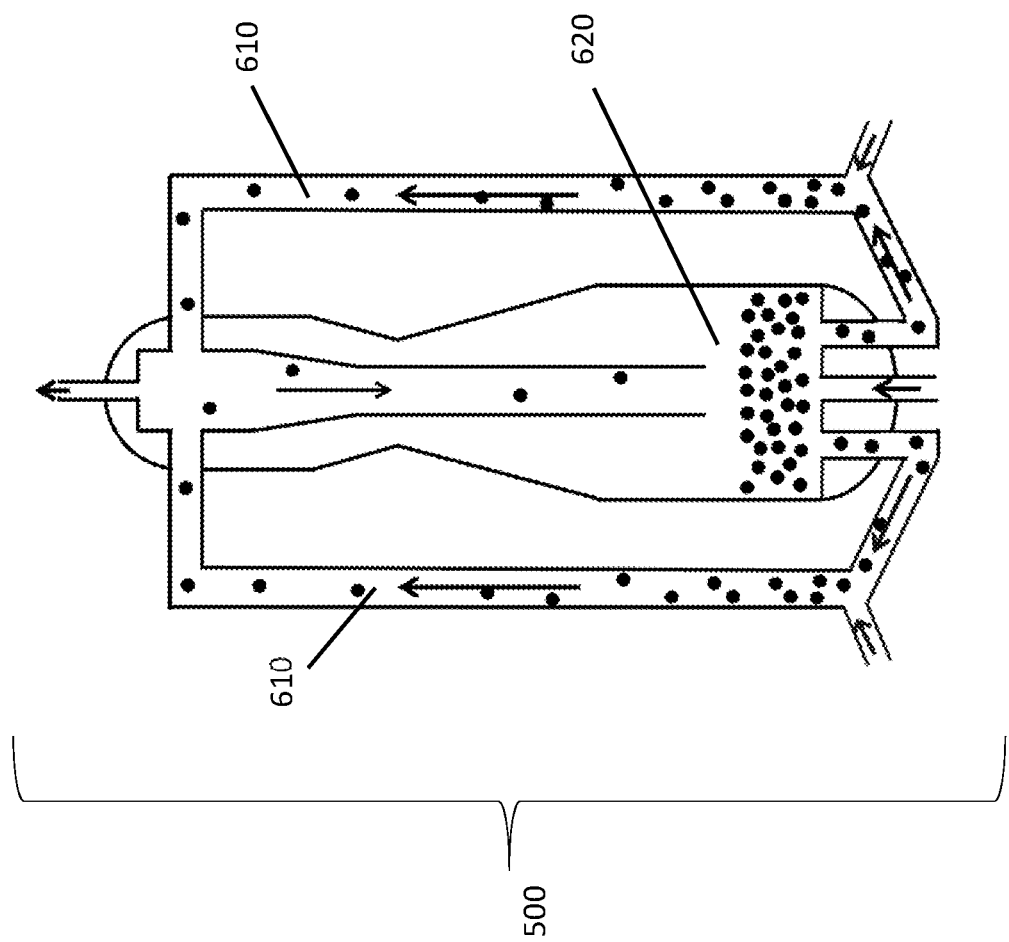
FIG. 10 illustrates a schematic of an embodiment of a system comprising a fluid bed reactor having two risers for cracking or cocracking of a hydrocarbon feed in accordance with aspects of the invention.

FIG. 10 illustrates a schematic of a non-limiting, exemplary embodiment of a system 600 comprising a fluid bed reactor that has two risers and is configured to facilitate contact of a hydrocarbon feed and the metal oxide. As illustrated in FIG. 10, system 600 includes a first riser configured for oxidative dehydrogenation of at least one alkane having a carbon chain of five or more and a second riser configured for oxidative dehydrogenation of at least one alkane having a carbon chain of four or less. The ratio of the alkane having a carbon chain of five or more to the alkane having a carbon chain of four or less may be set such that the overall reactor system is thermodynamically balanced or net exothermic. Some of the advantages of system 600 include that the reactor conditions, such as temperature, contact time, and pressure of the multiple reduction zones may be varied independently, thereby optimizing the overall yield of the desired products. Referring to FIG. 10, the hydrocarbon feed may be added to the regeneration zone 620 of the reactor, such that additional heat raises the temperature of the circulating oxygen transfer agent and/or metal oxide, thus supplying the necessary heat in oxidative cracking zone 610. In one embodiment, fuel comprising any organic material (including waste streams from other processes or carbon monoxide as long as the material reacts with oxygen) may be introduced into the reactor to produce heat/energy.

Additionally and/or alternatively, two different metal oxide reduction zones may be operated using different fluidization methods. As an example, one reactor zone could be a fixed or moving bed while the other a fluid bed, or any combination thereof. The multiple reduction zones may be particularly useful when methane is used as a hydrocarbon fuel to enhance the oxidative dehydrogenation cracking of the hydrocarbon feed.

EXAMPLES

The following examples are non-limiting embodiments of the present invention, included herein to demonstrate the advantageous utility obtained from aspects of the present invention.

Example 1

In Example 1, approximately 5 ml of metal oxide was charged to an alumina tube and the reactions were run at 650-750° C. at 1,200-2,400 $hr^{-1}$ GHSV. The experiments were run in this Example in a cyclic mode, whereby the reactor effluent of fifteen seconds of hydrocarbon feed was captured in a gas bag and analyzed by GC. After the reaction time, and subsequent reactor purge with nitrogen, air was flowed through the reactor bed for two minutes at the same temperature and flow rate as the hydrocarbon cycle. After a nitrogen purge, this sequence was repeated. The metal oxide was prepared by the addition of sufficient sodium nitrate via incipient wetness to yield 5% by weight of sodium on $Pr_6O_{11}$. After drying at 110° C., this material was calcined in air at 950° C. for twelve hours to form the metal oxide. Table 5, shown below, provides the results for the conversion of ethane at various parameters over the metal oxide or a combination of the metal oxide and a zeolite.

TABLE 5

| | | Example 1 | | | | |
|---|---|---|---|---|---|---|
| | | Catalyst | | | | |
| | | $Na/Pr_6O_{11}$ | | | | $Na/Pr_6O_{11}$ + ZSM-5 |
| | | Feed | | | | |
| | | Ethane | | | | Ethane |
| | | Temp., ° C. | | | | |
| | | 650 | 650 | 750 | 750 | 600 |
| | | GHSV, $hr^{-1}$ | | | | |
| | | 1,200 | 2,400 | 1,200 | 2,400 | 2,400 |
| % Selectivity | Methane | 1.19% | 5.65% | 4.28% | 3.27% | 5.07% |
| | Ethylene | 70.77% | 64.42% | 64.97% | 68.86% | 44.87% |
| | Acetylene | 0.00% | 0.00% | 0.13% | 0.07% | 0.00% |
| | Propylene | 1.55% | 1.23% | 2.72% | 2.25% | 4.83% |
| | Propadiene | 0.00% | 0.00% | 0.02% | 0.01% | 0.85% |
| | Propane | 0.78% | 0.60% | 1.20% | 1.04% | 0.00% |
| | Methyl Acetylene | 0.00% | 0.00% | 0.09% | 0.05% | 0.00% |
| | $C_4$'s | 17.44% | 21.12% | 0.01% | 6.77% | 1.67% |
| | $C_5$s | 2.29% | 2.02% | 2.12% | 2.06% | 0.15% |
| | $C_6^+$ | 4.76% | 3.06% | 2.95% | 2.46% | 1.33% |
| | Coke | N.D. | N.D. | N.D. | N.D. | N.D. |

TABLE 5-continued

Example 1

| | | Catalyst | | | | |
|---|---|---|---|---|---|---|
| | | Na/Pr$_6$O$_{11}$ | | | | Na/Pr$_6$O$_{11}$ + ZSM-5 |
| | | Feed | | | | |
| | | Ethane | | | | Ethane |
| | | Temp., °C. | | | | |
| | | 650 | 650 | 750 | 750 | 600 |
| | | GHSV, hr$^{-1}$ | | | | |
| | | 1,200 | 2,400 | 1,200 | 2,400 | 2,400 |
| | CO$_2$ | 1.21% | 1.89% | 21.04% | 13.17% | 40.52% |
| | CO | 0.00% | 0.00% | 0.47% | 0.00% | 0.71% |
| % Conversion | Feed | 15.60% | 8.44% | 78.20% | 62.13% | 9.91% |
| % Selectivity | Olefins | 97.60% | 92.45% | 74.21% | 83.56% | 53.71% |
| % Yield | Olefins | 15.22% | 7.80% | 58.03% | 51.92% | 5.32% |
| % Selectivity | % H$_2$ Selectivity | 0.00% | 0.00% | 2.41% | 7.18% | 10.38% |
| % Selectivity | % H$_2$O Selectivity | 100.00% | 100.00% | 97.59% | 92.82% | 89.62% |

This example demonstrates that Na/Pr$_6$O$_{11}$ is an effective metal oxide for producing olefins from oxidative dehydrogenation cracking of ethane. The selectivity to carbon containing products is calculated by dividing the carbon mole percent concentration of a particular product by the total concentration of all products. Yields are calculated by multiplying the total hydrocarbon conversion by the selectivity of the product. The moles of hydrogen produced, as analyzed by GC, is compare to the hydrogen contained in the carbon products. A stoichiometric deficit in the moles of hydrogen is assumed to be water. In the absence of a metal oxide, 100% selectivity to hydrogen is observed. Yields of olefins, which include ethylene, propylene, butylene and C5 olefins, were as high as 58%. These yields are comparable to steam cracking yields but were obtained at 100-150° C. lower temperatures. In addition, the oxidative dehydrogenation cracking reactions provide their own heat of reaction, as evidenced by the co-production of water, thus reducing the potential for both CO$_2$ and NOx emissions. Compared to the conversion of methane under similar conditions using Na/Pr$_6$O$_{11}$, the conversion of ethane was over three times higher. Additionally, it was discovered that a mixture of the metal oxide with a zeolite can greatly enhance the activity and yield of olefins from hydrocarbons. Accordingly, in Table 5 it is noted that a 50:50 by volume mixture of Na/Pr$_6$O$_{11}$ rare earth metal oxide catalyst with ZSM-5 produced almost 10% conversion of the ethane to olefins at temperatures as low as 600° C. This was highly unexpected.

Example 2

In Example 2, approximately 5 ml of metal oxide was charged to an alumina tube and the reactions were run at 650-750° C. at 1,200-2,400 hr$^{-1}$ GHSV. The experiments were run in this Example in a cyclic mode, whereby the reactor effluent from fifteen seconds of hydrocarbon feed was captured in a gas bag and analyzed by GC. After the reaction time, and subsequent reactor purge with nitrogen, air was flowed through the reactor bed for two minutes at the same temperature and flow rate as the hydrocarbon cycle. After a nitrogen purge, this sequence is repeated. Nitrogen concentration of hexane in the nitrogen was estimated to be 15-20%. The metal oxide comprising praseodymium was prepared by the addition of sufficient sodium nitrate via incipient wetness to yield 4% by weight of sodium on Pr$_6$O$_{11}$. After drying at 110° C., this material was calcined in air at 950° C. for twelve hours to produce the metal oxide. ZSM-5, which was purchased from Alfa-Aesar, was used as the ammonium salt and converted to the protonate form by calcination in air at 750° C. for twelve hours. The reactor bed was charged with a 50:50 weight percent mixture of the metal oxide and zeolite. Table 6, shown below, compares hexane pyrolysis in an empty alumina tube to oxidative dehydrogenation cracking of hexane over a metal oxide and a combination of metal oxide and zeolite.

TABLE 6

Example 2

| Feed | | n-Hexane | | |
|---|---|---|---|---|
| Temp., °C. | | 750 | 750 | 600 |
| Catalyst | | None | Na/Pr$_6$O$_{11}$ | Na/Pr$_6$O$_{11}$ + ZSM-5 |
| GHSV, hr$^{-1}$ | | 9,000 | 9,000 | 9,000 |
| % Selectivity | Methane | 11.20% | 9.58% | 3.18% |
| | Ethane | 3.77% | 2.75% | 10.02% |
| | Ethylene | 40.44% | 36.62% | 16.83% |
| | Acetylene | 0.00% | 0.08% | 0.03% |
| | Propylene | 24.69% | 18.44% | 28.98% |
| | Propadiene | 0.72% | 0.62% | 12.65% |
| | Propane | 0.13% | 0.05% | 0.00% |
| | Methyl Acetylene | 0.14% | 0.11% | 0.00% |
| | C$_4$'s | 15.16% | 17.34% | 17.07% |
| | C$_5$s | 3.73% | 3.74% | 1.53% |
| | Coke | N.D. | N.D. | N.D. |
| | CO$_2$ | 0.00% | 10.52% | 9.14% |
| | CO | 0.00% | 0.15% | 0.56% |
| % Conversion | Feed | 61.73% | 73.18% | 57.33% |
| % Selectivity | Olefins | 84.30% | 76.37% | 64.44% |
| % Yield | Olefins | 54.82% | 60.90% | 56.14% |
| % Selectivity | % H$_2$ Selectivity | 100.0% | 6.03% | 17.53% |
| % Selectivity | % H$_2$O Selectivity | 0.0% | 93.97% | 82.47% |

This example demonstrates that at comparable conditions, Na/Pr$_6$O$_{11}$ is more productive, and the mixture of Na/Pr$_6$O$_{11}$ and ZSM-5 is much more productive, for the conversion of hexane to olefins as compared to the empty tube control experiments. This conclusion is apparent by comparing the hexane conversions and contact times at similar temperatures. It should be noted that the use of a 50:50 mixture of Na/Pr$_6$O$_{11}$ with ZSM-5 demonstrated a hexane conversion at 600° C. that was comparable to the conversion of hexane produced by pyrolysis in an empty alumina tube at 750° C.

Although the invention is illustrated and described herein with reference to specific embodiments, the invention is not intended to be limited to the details shown. Rather, various modifications may be made in the details within the scope and range of equivalents of the claims and without departing from the invention. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method of producing one or more olefins by oxidative dehydrogenation cocracking of a hydrocarbon feed, the method comprising:
    cocracking a hydrocarbon feed comprised of at least one alkane having a carbon chain of five or more and at least one alkane having a carbon chain of four or less by contacting the hydrocarbon feed with a metal oxide, such that the cracking of the at least one alkane having a carbon chain of four or less produces one or more olefins and is exothermic, and the cracking of the at least one alkane having a carbon chain of five or more produces one or more olefins and is endothermic;
    utilizing the energy produced from the exothermic cracking of the at least one alkane having a carbon chain of four or less for the endothermic cracking of the at least one alkane having a carbon chain of five or more; and
    collecting a product from the cocracking of the hydrocarbon feed.

2. The method of claim 1, wherein cocracking of the hydrocarbon feed is performed at a temperature of greater than 500° C. and less than 1000° C. and wherein the product has a composition comprising at least 50% by weight of ethylene, propylene, or a combination thereof.

3. The method of claim 1, wherein cocracking of the hydrocarbon feed is performed at a temperature of greater than 600° C. and less than 850° C. and wherein the product has a composition comprising at least 40% by weight of ethylene, propylene, or a combination thereof.

4. The method of claim 1, wherein cocracking of the hydrocarbon feed is performed at a temperature of greater than 600° C. and less than 850° C. and wherein the product has a composition comprising at least 65% by weight of olefins.

5. The method of claim 1, wherein cocracking of the hydrocarbon feed is performed at a temperature of greater than 600° C. and less than 750° C. and wherein the product has a composition comprising at least 65% by weight of olefins.

6. The method of claim 1, wherein the at least one alkane having a carbon chain of four or less comprises ethane, and the at least one alkane having a carbon chain of five or more comprises naphtha.

7. The method of claim 6, wherein the hydrocarbon feed has a weight ratio of ethane to naphtha of from 3:10 to 9:10.

8. The method of claim 7, wherein the weight ratio of ethane to naphtha is from 3:10 to 6:10.

9. The method of claim 8, wherein the weight ratio of ethane to naphtha is from 3:10 to 4:10.

10. The method of claim 6, wherein the exothermic oxidative dehydrogenation of the at least one alkane having a carbon chain of four or less produces energy in a theoretical amount and the endothermic cracking of the at least one alkane having a carbon chain of five or more requires a theoretical amount of energy which ranges from 0% to 10% greater than the theoretical amount of energy produced by the exothermic oxidative dehydrogenation of the at least one alkane having a carbon chain of four or less.

11. The method of claim 1, where the metal oxide comprises at least one element selected from the group consisting of oxides of La, Ce, Pr, Tb, Nd, and Dy.

12. The method of claim 11, wherein the metal oxide further comprises at least one promoter selected from the group consisting of Na, Li, Ca, Mg, Sr, or Ba.

13. The method of claim 1, wherein the metal oxide for cocracking the hydrocarbon feed is comprised of oxides of Pr.

14. A method of producing one or more olefins by oxidative dehydrogenation cracking of a hydrocarbon feed comprising at least one alkane, the method comprising:
    cracking a hydrocarbon feed comprised of at least one alkane having a carbon chain of five or more by contacting the hydrocarbon feed with a metal oxide comprised of praseodymium oxide to produce one or more olefins; and
    collecting a product from the cracking of the hydrocarbon feed;
    wherein the hydrocarbon feed further comprises at least one alkane having a carbon chain of four or less to exothermically produce one or more olefins, the exothermic cracking of the at least one alkane having a carbon chain of four or less produces a theoretical amount of energy, and the endothermic cracking of the at least one alkane having a carbon chain of five or more requires a theoretical amount of energy which is greater than the theoretical amount of energy produced by the exothermic oxidative dehydrogenation of the at least one alkane having a carbon chain of four or less.

15. The method of claim 14, wherein the metal oxide further comprises at least one promoter selected from the group consisting of Na, Li, Ca, Mg, Sr, or Ba.

16. The method of claim 15, wherein the metal oxide is employed in combination with a zeolite.

17. The method of claim 16, wherein the zeolite has a composition in accordance with general formula: $M_{2/n}O.Al_2O_3.ySiO_2.wH_2O$, where y varies from 2 to 1,000,000,000, M is a positively charge element for balancing the charged of the zeolite and may include protons, alkaline metals, alkaline earth metals or other elements known to those skilled in the art, n represents the cation valence and w represents the number of water molecules per zeolite unit structure, such that, at least 5% of n is due to proton charge.

18. The method of claim 16, wherein the zeolite has a composition in accordance with general formula: $M_{2/n}O.Al_2O_3.ySiO_2.wH_2O$ where y is from 4 to 35, M is a positively charged element for balancing the charge of the zeolite and may include protons, alkaline metals, alkaline earth metals or other elements known to those skilled in the art, n represents the cation valence and w represents the number water molecules per zeolite unit structure, such that, at least 5% of n is due to proton charge.

19. The method of claim 16, wherein the zeolite is ZSM-5.

* * * * *